United States Patent
Okada et al.

(10) Patent No.: US 7,988,957 B2
(45) Date of Patent: Aug. 2, 2011

(54) GENE INTRODUCTION EFFICIENCY ENHANCER

(75) Inventors: Takashi Okada, Tochigi (JP); Keiya Ozawa, Tochigi (JP)

(73) Assignee: Genesis Healthcare Corp., Tokyo (JP)

( * ) Notice: Subject to any disclaimer, the term of this patent is extended or adjusted under 35 U.S.C. 154(b) by 791 days.

(21) Appl. No.: 10/554,246

(22) PCT Filed: Apr. 9, 2004

(86) PCT No.: PCT/JP2004/005166
§ 371 (c)(1),
(2), (4) Date: Dec. 11, 2006

(87) PCT Pub. No.: WO2004/096289
PCT Pub. Date: Nov. 11, 2004

(65) Prior Publication Data
US 2008/0214446 A1 Sep. 4, 2008

(30) Foreign Application Priority Data
Apr. 25, 2003 (JP) .................................. 2003-122968

(51) Int. Cl.
*A61K 48/00* (2006.01)
*C12Q 1/68* (2006.01)
(52) U.S. Cl. .......................... 424/93.1; 435/6; 514/44 R
(58) Field of Classification Search .................. None
See application file for complete search history.

(56) References Cited

U.S. PATENT DOCUMENTS
6,410,300 B1 * 6/2002 Samulski et al. ............. 435/239

FOREIGN PATENT DOCUMENTS
WO    WO 974707    * 12/1997 ................. 435/6

OTHER PUBLICATIONS

M. Jung. Current Med. Chem. (2001) 8, 150-1511.*
M.E. Goldsmith et al. Clin. Cancer Res. (2003) 9, pp. 5394-5401.*
H. J. Kwon et al. Int. J. Cancer (2002) 97, pp. 290-296.*
G. Rajgolikar et al. Recent Cancer Res. Treat. (1998) 51, pp. 20-38.*
M. Murata et al. Jpn. J. Cancer Res. (2000) 91, pp. 1154-1160.*
R. Furumai et al. Cancer Res. (2002) 62, pp. 4916-3921.*
R.R. Frey et al. Bioorg. Med. Chem. Let. (2002) 12, pp. 3443-3447.*
Nakajima et al. Experimental Cell Research 241, 126-133 (1998).*
Alisky et al. Human Gene Therapy 11:2315-2329 (Nov. 20, 2000).*
Takashi Okada et al.; "A Histone Deacetylase Inhibitor Enhances Recombinant Adeno-associated Virus-Mediated Gene Expression in Tumor Cells"; Nov. 2005; pp. 1-9; Division of Genetic Therapeutics, Center for Molecular Medicine, Tochigi, Japan.
Wen Yong Chen et al., "Reactivation of Silenced, Virally Transduced Genes by Inhibitors of Histone Deacetylase"; Proc. Natl. Acad. Scie. USA, vol. 94, pp. 5798-5803, 1997.
Masaki Kitazono et al.; "Enhanced Adenovirus Transgene Expression in Malignant Cells Treated with the Histone Deacetylase Inhibitor"; FR901228; Cancer Research; vol. 61, pp. 6328-6330; 2001.
L. David Dion; "Amplification of Recombinant Adenoviral Transgene Products Occurs by Inhibition of Histone Deacetylase"; Virology; vol. 231, pp. 201-209; 1997.
Kenneth Lundstron; "Latest Development in Viral Vectors for Gene Therapy"; Trends in Biotechnology; vol. 21, No. 3; Mar. 2003.
Genevieve Almousni et al.; "Histone Acetylation Influences Both Gene Expression and Development of *Xenopus laevis*"; Developmental Biology; vol. 165, pp. 654-669; 1994.

* cited by examiner

*Primary Examiner* — Doug Schultz
(74) *Attorney, Agent, or Firm* — Bacon & Thomas, PLLC

(57) ABSTRACT

A gene transfer efficiency enhancer of the present invention which contains a histone deacetylase inhibitor (especially compound (A)) as an active ingredient is capable of enhancing gene transfer efficiency in a gene transfer mediated by an adeno-associated virus vector while retaining the advantages of the adeno-associated virus vector.

15 Claims, 2 Drawing Sheets

GENE INTRODUCTION EFFICIENCY ENHANCER

The present invention relates to an agent capable of increasing the gene transfer efficiency in gene transfer mediated by an adeno-associated virus vector (hereinafter may be referred to as an "AAV vector"). More particularly, the present invention relates to an enhancer for increasing the efficiency of AAV-vector-mediated gene transfer, the enhancer containing a compound having histone deacetylase inhibitory activity.

BACKGROUND ART

Gene therapy has been considered effective means for treating intractable diseases, and 600 or more gene therapy protocols have already been proposed in different countries (mainly in Europe and the United States).

As has been known, vectors which are currently employed in gene therapy include adenovirus vectors and retrovirus vectors and so on. However, adenoviruses have been shown to cause severe inflammation in the liver or the brain in clinical studies, whereas retroviruses raise problems including insertion mutation resulting from random integration into chromosomal DNA, and induction of cancer associated therewith.

Meanwhile, adeno-associated virus (hereinafter may be abbreviated as "AAV") vectors have the following characteristics: 1) being nonpathogenic, 2) having low immunoreactivity, 3) capable of transferring a gene into nondividing cells, and 4) enabling long-term transgene expression. Particularly, AAV vectors exhibit excellent safety as compared with, for example, the aforementioned retrovirus vectors or adenovirus vectors. In recent years, vectors based on various AAV serotypes (e.g., AAV serotypes 1 to 5) have been developed. Such AAV serotype vectors enable gene expression in various tissues on the basis of the difference in infection targets between these AAV serotypes. By virtue of the aforementioned characteristics, AAV vectors have been considered promising vectors for gene therapy. For example, conventionally, AAV vectors have generally been employed for protein replacement therapy through intramuscular administration. However, AAV vectors, which have low gene transfer efficiency (particularly in the case of gene transfer into cancer cells), have become of less interest in cancer therapy, which requires that a therapeutic gene be transferred into all the cells.

As has been reported, when an adenovirus vector is employed, expression an adenovirus receptor (integrin or CAR (coxsackievirus adenovirus receptor)) is increased by a histone deacetylase inhibitor, and transgene expression is enhanced. Meanwhile, it has been reported that when an AAV vector is employed, a histone deacetylase inhibitor reactivates transgene expression in cells which have been infected and then subcultured for a long period of time, in which the genome is integrated and is in a non-expression state (see, for example, Chen, et al., Proceedings of the National Academy of Sciences USA, Vol. 94, pp. 5798-5803 (1997)).

In gene therapy employing an AAV vector, a effective target is not reactivation of cells which are in a non-expression state, but the efficiency of the AAV vector-mediated gene transfer into cells (in an expression state). However, studies on such gene transfer efficiency have not yet been conducted.

DISCLOSURE OF THE INVENTION

An object of the present invention is to overcome the drawback of AAV vectors (i.e., low gene transfer efficiency), which has conventionally prevented application of the vectors, while maintaining advantages of the vectors. Another object of the present invention is to provide an enhancer for increasing the gene transfer efficiency in gene transfer (hereinafter the enhancer may be referred to as a "gene transfer efficiency enhancer"), which enhancer can be employed as a pharmaceutical drug, and can be suitably employed for gene therapy, particularly for cancer gene therapy.

It has generally been considered that when an AAV vector is employed, conversion of vector genome into an expression form is more important for gene expression than virus uptake into cells, and gene expression is less envisaged to be affected by merely enhancement of receptor expression by means of a histone deacetylase inhibitor. However, surprisingly, the present inventors have discovered that when a gene is transferred into cells by means of an AAV vector, if a histone deacetylase inhibitor is employed in combination with the vector, the efficiency of the gene transfer is increased considerably. In this case, a change in enhancement of integrin expression is smaller than a change in the gene transfer efficiency, and no significant difference is observed in transgene copy number between a histone-deacetylase-inhibitor-treated group and a non-treated group.

On the basis of the above knowledge, the present inventors have found that a histone deacetylase inhibitor increases the efficiency of AAV-vector-mediated gene transfer by a mechanism different from that which has conventionally been reported, in which a histone deacetylase inhibitor reactivates a transgene which exhibits reduced expression after being integrated into chromosomes. The present invention has been accomplished on the basis of this finding.

Accordingly, the present invention provides the following.
(1) An enhancer for increasing the gene transfer efficiency in a gene transfer mediated by an adeno-associated virus vector, the enhancer containing a histone deacetylase inhibitor as an active ingredient.
(2) An enhancer as described in (1) above, wherein the histone deacetylase inhibitor is a compound represented by formula (I):

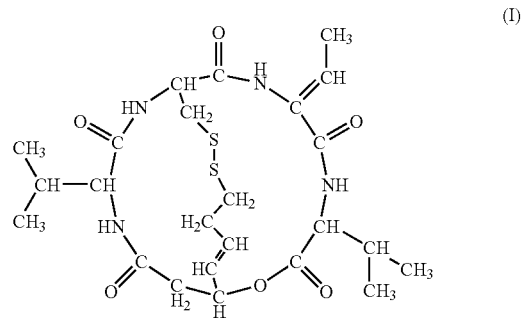

or a salt of the compound.
(3) An enhancer as described in (1) or (2) above, wherein the gene transfer is performed to tumor cells.
(4) An enhancer as described in any one of (1) through (3) above, which is a pharmaceutical drug.
(5) An enhancer as described in (4) above, wherein the pharmaceutical drug is for gene therapy.
(6) An enhancer as described in (5) above, wherein the gene therapy is performed against cancer.
(7) A method for increasing the gene transfer efficiency in a gene transfer mediated by an adeno-associated virus vector, the method comprising administering an effective dose of a histone deacetylase inhibitor to a subject in need of an increase in the gene transfer efficiency in a gene transfer mediated by an adeno-associated virus vector.

(8) A method as described in (7) above, wherein the histone deacetylase inhibitor is a compound represented by formula (I) or a salt of the compound.

(9) A method as described in (7) or (8) above, wherein the gene transfer is performed to tumor cells.

(10) A method as described in any one of (7) through (9) above, which is performed for gene therapy.

(11) A method as described in (10) above, wherein the gene therapy is performed against cancer.

(12) Use of a histone deacetylase inhibitor for producing an enhancer for increasing the gene transfer efficiency in a gene transfer mediated by an adeno-associated virus vector.

(13) Use as described in (12) above, wherein the histone deacetylase inhibitor is a compound represented by formula (I) or a salt of the compound.

(14) Use as described in (12) or (13) above, wherein the gene transfer is performed to tumor cells.

(15) Use as described in any one of (12) through (14) above, wherein the enhancer for increasing the gene transfer efficiency in a gene transfer mediated by an adeno-associated virus vector is a pharmaceutical drug.

(16) Use as described in (15) above, wherein the pharmaceutical drug is for gene therapy.

(17) Use as described in (16) above, wherein the gene therapy is performed against cancer.

(18) A commercial package comprising an enhancer as described in any one of (1) through (6) above, and a package insert describing whether the enhancer can be used or is suggested to be used for gene therapy.

(19) A package described in (18) above, wherein the gene therapy is performed against cancer.

BRIEF DESCRIPTION OF THE DRAWINGS

FIG. 1A shows the percent occurrence (%) of CD51-positive cells in the case where U251MG is treated with FK228 of different concentrations. FIG. 1B shows the percent occurrence (%) of EGFP (transgene)-positive cells in the case of gene transfer by use of an AAV vector in combination with FK228.

DETAILED DESCRIPTION OF THE INVENTION

Figure 1:
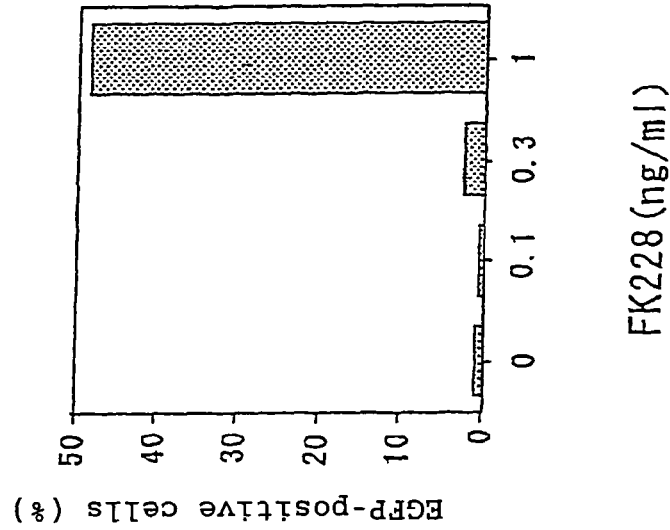
FIG. 1 is a set of graphs showing the relation between the effect of FK228 on CD51 (integrin) expression and the effect of FK228 on enhancement of transgene expression.
Figure 1:

As used herein, the term "histone deacetylase inhibitor" refers to a compound which binds to the active site of histone deacetylase competitively with a substrate of the enzyme, or a compound having an activity of binding to a site of histone deacetylase other than the active site thereof, thereby changing the enzyme activity of histone deacetylase. Examples of the histone deacetylase inhibitor include such compounds which have already been known and employed as histone deacetylase inhibitors; all compounds (synthetic and naturally occurring compounds) which have heretofore been reported to have histone deacetylase inhibitory activity; and all compounds which in the future will be reported to have such activity. Specific examples of the histone deacetylase inhibitor include a compound having a structure represented by the below-described formula (I) (hereinafter the compound may be referred to simply as "compound A"; SEQ ID NO: 1), salts of the compound, and derivatives of the compound (e.g., a derivative obtained through acetylation of compound A, and a thiol derivative obtained through reduction of the S—S bond of compound A). Examples of compounds which have been reported to have histone deacetylase inhibitory activity include trichostatin A, sodium butyrate, suberoylanilide hydroxamic acid (SAHA), MS-275, cyclic hydroxamic-acid-containing peptide, apicidin, and trapoxin.

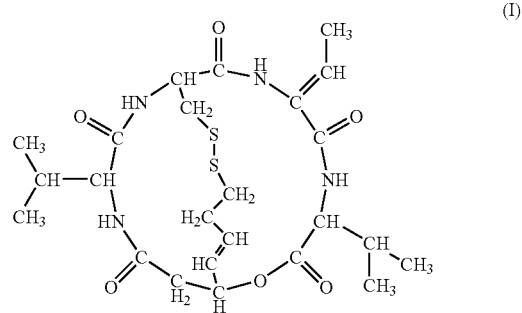

(I)

Compound A may have stereoisomers (e.g., optical isomers and geometric isomers) due to asymmetric carbon atoms and carbon-carbon double bonds; for example, FK228 represented by the below-described formula (II). As used herein, "the histone deacetylase inhibitor" encompasses all of these isomers of compound A and mixtures thereof.

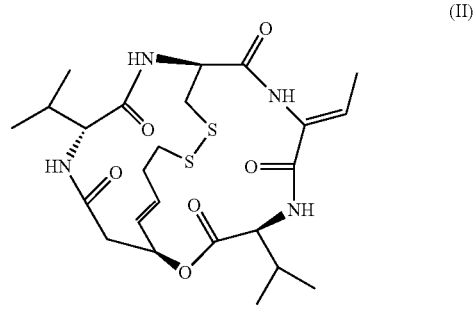

(II)

As used herein, "the histone deacetylase inhibitor" also encompasses solvates (e.g., clathrate compounds (e.g., hydrates)) of compound A, FK228, salts of compound A, and salts of FK228.

As used herein, unless otherwise specified, the term "compound A" refers to a compound belonging to the group consisting of all stereoisomers of compound A, including a compound represented by formula (II) (FK228).

Compound A or a salt thereof is a known and available substance. For example, FK228, which is one of stereoisomers of compound A, can be prepared through the following procedure: a strain which belongs to the genus *Chromobacterium* and which can produce FK228 is cultured under aerobic conditions, and FK228 is recovered from the resultant culture broth. Examples of the strain which belongs to the genus *Chromobacterium* and which can produce FK228 include *Chromobacterium violaceum* WB968 (FERM BP-1968). More specifically, FK228 can be prepared from the aforementioned production strain as described in Japanese Patent Publication (kokoku) No. 7-64872 (U.S. Pat. No. 4,977,138). FK228 is preferably recovered from a strain which belongs to the genus *Chromobacterium* and which can produce FK228, from the viewpoint of easy preparation of FK228. Also, FK228 is preferably prepared through synthesis or semisynthesis, from the viewpoint that no further purification processes are required, or purification processes can be reduced. Similar to the case of FK228, compound A other than FK228 can be prepared through semisynthesis or total synthesis according to a conventionally known method. More specifically, such compound A can be produced through the method reported by Khan W. Li, et al. (J. Am. Chem. Soc., Vol. 18, 7237-7238 (1996)).

Examples of salts of compound A include base salts and acid addition salts, including inorganic base salts such as alkali metal salts (e.g., sodium salts and potassium salts), alkaline earth metal salts (e.g., calcium salts and magnesium salts), and ammonium salts; organic base salts such as organic amine salts (e.g., triethylamine salts, diisopropylethylamine salts, pyridine salts, picoline salts, ethanolamine salts, triethanolamine salts, dicyclohexylamine salts, and N,N'-dibenzylethylenediamine salts); inorganic acid addition salts (e.g., hydrochlorides, hydrobromides, sulfates, and phosphates); organic carboxylic acid addition salts and sulfonic acid addition salts (e.g., formates, acetates, trifluoroacetates, maleates, tartrates, fumarates, methanesulfonates, benzenesulfonates, and toluenesulfonates); and salts with basic and acidic amino acids (e.g., arginine, aspartic acid, and glutamic acid).

In the present invention, examples of the subject in need of an increase in the efficiency of (foreign) gene transfer include various animals such as human, mouse, rat, pig, dog, horse, cattle, and monkey; and cells of such an animal. As used herein, the expression "enhancement of transgene expression" refers to enhancement of expression of a foreign gene in a host cell, the gene being transferred through a genetic engineering technique. Expression of the transgene may be enhanced at the cellular level or at the animal level. As used herein, the expression "an increase in the gene transfer efficiency in a gene transfer" refers to an increase in the percentage of AAV-vector-mediated foreign gene transfer into cells.

According to the present invention, a gene can be efficiently transferred into cells (in particular, tumor cells) by means of an AAV vector. The AAV-vector-mediated gene transfer enables safe and stable expression of the transferred gene.

An AAV vector carrying a target foreign gene is prepared by inserting the gene into a wild-type AAV. For example, such an AAV vector is prepared through the following procedure. Firstly, a target gene is inserted between ITRs present at the both ends of a wild-type AAV, to thereby prepare a plasmid (AAV vector plasmid). Separately, a helper-virus-derived helper plasmid is provided for supplying a viral protein required for viral replication or viral particle formation. Subsequently, both the plasmids are introduced into, for example, 293 cells through transfection, and the cells are infected with the helper virus, to thereby prepare a recombinant AAV vector. More specifically, such vector preparation can be performed according to, for example, the following references.

Reference 1: Okada T, Nomoto T, Shimazaki K, Wang L, Lu Y, Matsushita T, Mizukami H, Urabe M, Hanazono Y, Kume A, Muramatsu S, Nakano I, Ozawa K. "Adeno-associated virus vectors for gene transfer to the brain." Methods 2002; 8: 237-247.

Reference 2: Okada T, Shimazaki K, Nomoto T, Matsushita T, Mizukami H, Urabe M, Hanazono Y, Kume A, Tobita K, Ozawa K, Kawai N. "Adeno-associated viral vector-mediated gene therapy of ischemia-induced neuronal death." Methods Enzymol 2002; 346: 378-393.

AAV per se has no replication ability, and thus AAV replication requires a helper virus. However, a system which does not require a helper virus has been recently available through, for example, modification of a helper plasmid. The present invention encompasses a mode employing such a system.

The gene transfer efficiency enhancer of the present invention can be used in the form of a solid, semisolid, or liquid drug product containing a mixture of a histone deacetylase inhibitor serving as an active ingredient (e.g., compound A or a salt thereof) and an organic or inorganic carrier (or excipient) suitable for oral or parenteral administration. The active ingredient may be mixed with a typical nontoxic and pharmaceutically acceptable carrier suitable for preparation of, for example, a powder, a tablet, a pellet, a capsule, a suppository, a solution, an emulsion, a suspension, an aerosol, or a spray. If desired, an auxiliary agent, a stabilizer, a thickener, or the like may also be employed. If desired, such a carrier or excipient may be subjected to sterilization treatment before being mixed with the active ingredient. Alternatively, such sterilization treatment may be performed after preparation of a drug product. Compound A or a salt thereof is incorporated into the gene transfer efficiency enhancer in an amount sufficient for causing an intended effect on a subject in need of an increase in the efficiency of gene transfer.

No particular limitation is imposed on the administration method for the gene transfer efficiency enhancer of the present invention, which contains a histone deacetylase inhibitor as an active ingredient, so long as expression of a gene transferred by means of an AAV vector is enhanced.

In the case where the gene transfer efficiency enhancer is employed in the form of a drug product, the enhancer can be orally or parenterally administered once to several times a day. Particularly when the enhancer is employed for gene therapy, preferably, the enhancer is administered parenterally (e.g., intravenous administration, intraarterial administration, intramuscular administration, direct interstitial administration, intranasal administration, intradermal administration, cerebrospinal fluid administration, intraductal administration, or intravaginal administration).

The therapeutically effective dose of the active ingredient varies depending on the type of a histone deacetylase inhibitor to be employed, the age and pathological conditions of a patient to be treated, the type of a transgene, and the type of a disease requiring enhancement of expression of the gene. Therefore, the therapeutically effective dose is determined in consideration of such factors.

For example, in the case of continuous intravenous administration of compound A serving as a histone deacetylase inhibitor, the daily dose (once a day) for an adult is preferably 1 mg/m$^2$ to 50 mg/m$^2$, more preferably 3 mg/m$^2$ to 30 mg/m$^2$.

A characteristic feature of the gene transfer efficiency enhancer of the present invention resides in that the enhancer increases the efficiency of gene transfer, and thus enhances expression of the transgene. Interaction between the enhancer and the transgene is an important factor for attaining such effects. Therefore, the timing of administration of a foreign gene and the timing of administration of the gene transfer efficiency enhancer of the present invention are appropriately determined in accordance with intended effects. For example, in the case where expression of a foreign gene is to be enhanced, preferably, the enhancer of the present invention is administered simultaneous with, before, or after administration of the foreign gene, whose expression is to be enhanced.

The timing of administration of the enhancer of the present invention may be appropriately determined in accordance with intended effects or the extent of the effects. However, in view of the purpose and effects of the enhancer of the present invention; i.e., increasing the efficiency of AAV-vector-mediated foreign gene transfer, and enhancing expression of the transgene (not reactivation of the transgene), preferably, the enhancer of the present invention is administered simultaneous with, immediately before, or immediately after AAV-vector-mediated gene transfer.

In a mode of the present invention, when the gene transfer efficiency enhancer of the present invention is employed for cancer gene therapy, in anticipation of the antitumor effect and the gene transfer efficiency increasing effect of a histone deacetylase inhibitor serving as an active ingredient, the gene transfer efficiency enhancer can be administered before or after administration of an AAV vector (including a target foreign gene).

The foreign gene to be transferred may be any gene, so long as expression of the gene is intended. Examples of the foreign gene to be transferred include a variety of genes employed for gene therapy. Specific examples include cytosine deaminase gene, herpes simplex virus thymidine kinase (HSV-TK) gene, and Bim-S gene (see Gene Ther. Mar. 10, 2003 (5): 375-385).

The enhancer of the present invention can be suitably employed particularly for gene therapy. For example, cancer gene therapy employs suicide gene transfer or a DNA vaccine. Examples of the suicide gene transfer include transfer of a gene encoding cytosine deaminase, which is an enzyme for converting 5-fluorocytosine (5-FC) (i.e., an anticancer drug) into an active form, into cancer cells. Expression of the gene in cancer cells can be enhanced by means of the enhancer of the present invention (i.e., 5-FC is efficiently converted into an active form in a cancer-cell-specific manner, thereby inducing the antitumor effects of the drug). Alternatively, herpes simplex virus thymidine kinase (HSV-TK) gene is transferred into cancer cells, and subsequently ganciclovir (GCV), which is an antiviral drug, is administered. GCV phosphorylated by HSV-TK inhibits DNA synthesis in the cancer cells, whereby antitumor effects are obtained.

Examples of the DNA vaccine to be employed include cancer antigen genes which express specifically in cancer cells. Through transfer of such a gene into a cancer patient, through reactivation of an endogenous cancer antigen gene whose expression is suppressed, or through both, expression of the cancer antigen gene can be enhanced, thereby enhancing immunity of the patient to cancer.

Cancer gene therapy may employ, in addition to the aforementioned genes, p53 gene, cytokine gene (e.g., IL2 gene and IL12 gene), antisense gene (e.g., EGFR antisense gene, SDF-1 antisense gene, or K-ras antisense gene), siRNA, etc. Gene therapy for cystic fibrosis may employ CFTR gene, and gene therapy for hemophilia may employ coagulation factor gene.

As described above, the gene transfer efficiency enhancer of the present invention, which contains a histone deacetylase inhibitor as an active ingredient, is useful for cancer gene therapy. Since the histone deacetylase inhibitor per se is envisaged to exhibit anticancer effects, use of the enhancer of the present invention for cancer therapy is further preferred. Particularly when compound A is employed, its anticancer effects can be further enhanced by gene therapy employing an AAV vector, which is preferred.

The gene transfer efficiency enhancer of the present invention, which contains a histone deacetylase inhibitor as an active ingredient, is also envisaged to exhibit its effects in various tissues or organs. Examples of the effects of the enhancer include the effect of enhancing expression of a transgene in muscles or neurons. Thus, the gene transfer efficiency enhancer increases the efficiency of foreign gene transfer in various tissues or organs, and therefore, the enhancer is considered useful for gene therapy for, for example, neuromuscular diseases (e.g., myotonic dystrophy and amyotrophic lateral sclerosis (ALS)), heart failure, cardiomyopathy, diseases treated with protein supplementation therapy through expression of a secretory protein (e.g., chronic systemic diseases such as arteriosclerosis, hypertension, heart failure, diabetes, and hyperlipidemia), cerebral infarction, reperfusion injury after cerebral ischemia, Parkinson's disease, various neurodegenerative diseases, mitochondrial encephalomyopathy, epilepsy, schizophrenia, and alcoholism.

The gene transfer efficiency enhancer is also useful for gene transfer into ES cells or hematopoietic stem cells.

The gene to be transferred may be appropriately varied in accordance with the disease to be targeted.

The gene transfer efficiency enhancer of the present invention may be included in a commercial package together with a package insert describing that the enhancer increases the gene transfer efficiency in a gene transfer mediated by an adeno-associated virus vector, particularly a package insert describing that the enhancer is suggested to be used for cancer gene therapy. The commercial package may further include a necessary reagent or instrument.

EXAMPLES

The present invention will next be specifically described in detail by way of Examples, which should not be construed as limiting the invention thereto. Unless otherwise specified, the following test materials are employed in the Examples.

Test Materials

1. Drug

FK228 which had been isolated and purified through the method described in Japanese Patent Publication (kokoku) No. 7-64872 was employed as a histone deacetylase inhibitor. The FK228 was dissolved in ethanol for storage. When in use, the FK228 was diluted with a medium, to thereby regulate the FK228 concentration to fall within a range of 0 to 100 ng/mL.

2. Vector

An AAV vector genome plasmid and a helper plasmid were introduced into 293 cells through the calcium phosphate method, and AAV vectors (types 1 to 5) which express EGFP (enhanced green fluorescent protein) under the control of a cytomegalovirus (CMV) promoter were prepared. Specifically, the AAV vector preparation was performed through the method described in the following references.

Reference 1: Methods 2002; 8: 237-247 (described above)

Reference 2: Methods Enzymol 2002; 346: 378-393 (described above)

3. Cells and Cell Culture (1) Human Glioma Cell Line; U251MG, U87MG

U251MG was obtained from JCRB Cell Bank, National Institute of Health Sciences. U251MG cells were cultured in an Eagle's MEM (minimum essential medium) containing 10% fetal bovine serum (FBS) at 5% $CO_2$ and 37° C. U87MG was obtained from Institute for Fermentation, Osaka. U87MG cells were cultured in an Eagle's MEM containing 10% FBS at 5% $CO_2$ and 37° C.

(2) Rat Glioma Cell Line; 9L 9L was obtained from American Type Culture Collection (ATCC). 9L cells were cultured in a DMEM (Dulbecco's modified Eagle's medium) containing 10% FBS at 5% $CO_2$ and 37° C.

(3) Human Head and Neck Cancer Cell Line; HEp-2

HEp-2 was obtained from Cell Resource Center for Biomedical Research, Institute of Development, Aging and Cancer, Tohoku University. HEp-2 cells were cultured in an Eagle's MEM containing 10% FBS at 5% $CO_2$ and 37° C.

(4) Subcultured Human Glioma Cells (Operative Specimen)

The cells, which were prepared from an operative specimen, are positive for GFAP (glial fibrillary acidic protein) and vimentin, and are considered to be derived from glioma through pathological diagnosis.

Example 1

Effect of FK228 on the Efficiency of AAV-Vector-Mediated Gene Transfer

The effect of FK228 on enhancing expression of a transgene was evaluated with glioma cells. Type-2 AAV vector ($1\times10^4$ genome copies/cell) and FK228 (0, 0.01, 0.1, 1, 10, or 100 ng/mL) were added to a culture supernatant of the human glioma cell line U251MG, and 24 hours later, expression of EGFP was observed under a fluorescence microscope. Through this observation, expression of EGFP was found to be enhanced in an FK228-dose-dependent manner. Particularly when added at a concentration of 1 ng/mL or more, FK228 exhibited remarkable EGFP expression enhancing effect.

The fact that the enhancer of the present invention exhibited gene expression enhancing effect within 24 hours after gene transfer (infection) suggests the possibility that the episomal AAV genome which had not undergone chromosomal integration underwent histone modification, whereby its gene expression was regulated and enhanced.

Similar to the case of U251MG, in the cases of the head and neck cancer cell line HEp-2 and the subcultured human glioma cells (prepared from an operative specimen), the effect of FK228 in enhancing AAV-vector-mediated gene transfer was evaluated. In both cases, EGFP expression was found to be enhanced through addition of FK228 (1 ng/mL); i.e., the enhancer of the present invention exhibited gene transfer efficiency increasing effect.

Example 2

Relation Between the Effect of FK228 on Increasing Gene Transfer Efficiency and Integrin Expression The gene expression enhancing effect obtained by employment of an adenovirus vector in combination with a histone deacetylase inhibitor is considered to be based on the mechanism that expression of a receptor such as integrin is enhanced by the histone deacetylase inhibitor. Tests were performed to assess whether or not such a mechanism is involved in the effects of the present invention.

Type-2 AAV vector ($1\times10^4$ genome copies/cell) and FK228 (0, 0.01, 0.1, or 1 ng/mL) were added to a culture supernatant of U251MG, and 24 hours later, the percent occurrence of cells positive for CD51 (integrin) or EGFP was calculated through FACS analysis. The FACS analysis was performed through a customary method by use of FACSCan (Becton Dickinson, San Jose, Calif.) and CellQuest software (Becton Dickinson, San Jose, Calif.).

PE-labeled anti-CD51 monoclonal antibody: 13C2 was obtained from Cymbus Biotechnology Ltd., Chandlers Ford, UK. Dead cells were detected by means of 7-amino-actinomycin D (Via-Probe; Pharmingen, San Diego, Calif.).

Cells were washed with a FACS buffer (PBS containing 5% FBS and 0.05% sodium azide), and then incubated with the antibody on ice for 30 minutes. Fluorescences attributed to EGFP, PE, and Via-Probe were detected by FL1, FL2, and FL3, respectively. Cells negative for Via-Probe; i.e., viable cells, were employed for measuring expression of EGFP and/or CD51.

The percent occurrence of EGFP-positive cells was sharply increased through addition of FK228 (1 ng/mL). In contrast, the percent occurrence of integrin-positive cells shows a gradual increase. The results are shown in FIG. 1.

The results indicate that the effect of FK228 in increasing gene transfer efficiency is not based on the mechanism by which FK228 increases the number of receptors on cell surfaces.

Example 3

Effect of FK228 Addition on the Number of Viral Genome Copies Taken into Cells

Figure 2:
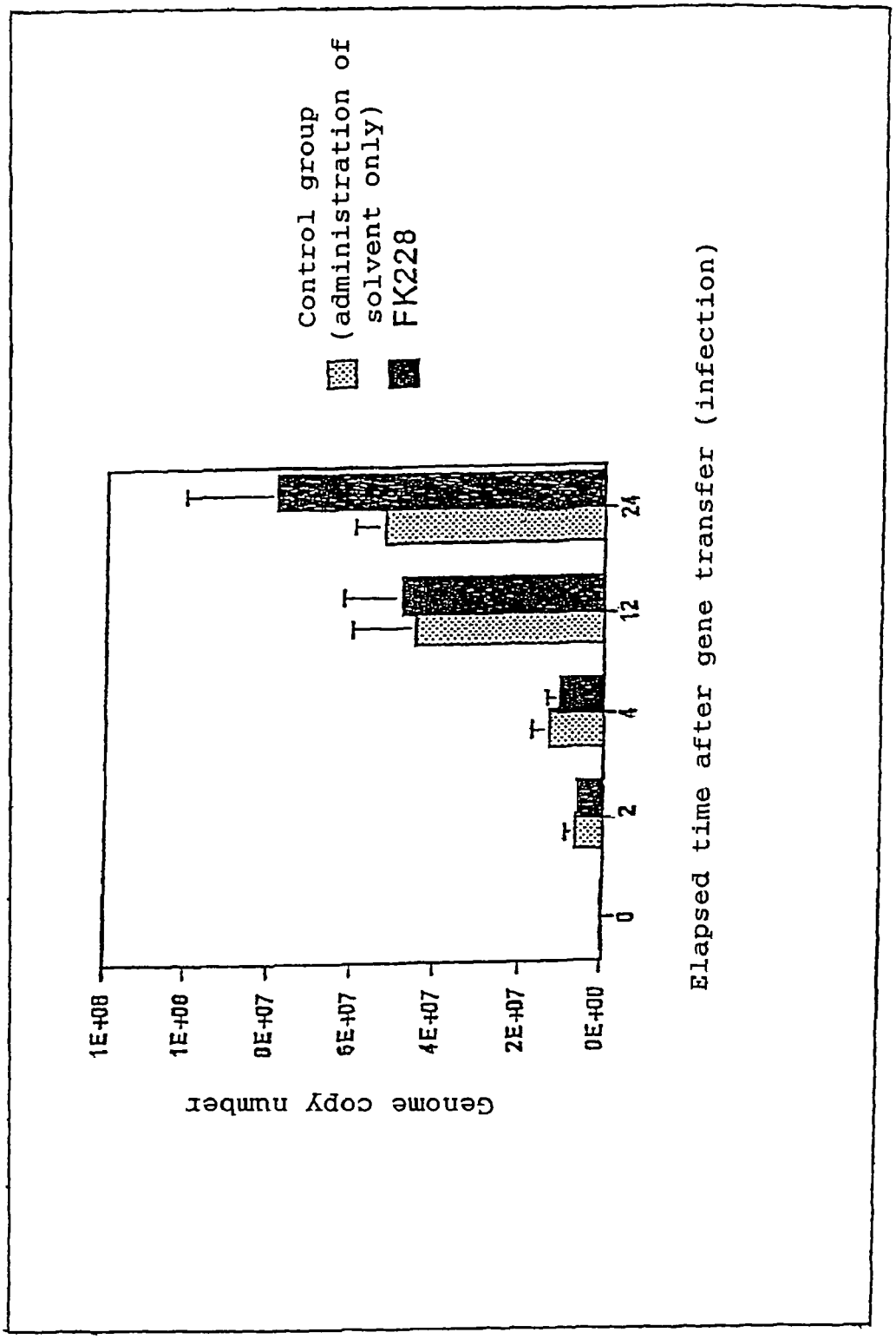
FIG. 2 is a graph showing the effect of FK228 on the number of viral genome copies taken into cells. The vertical axis corresponds to the genome copy number, and the horizontal axis corresponds to the elapsed time after infection.

Type-2 AAV vector ($1\times10^4$ genome copies/cell) and FK228 (1 ng/mL) were added to a culture supernatant of U251MG, and the number of viral genome copies taken into cells was semi-quantified by means of real-time PCR (ABI, Prism 7700; QIAGEN, SYBR Green PCR kit QuantiTect) (performed through the method according to Mol. Ther. Aug. 6, 2002 (2): 272-278). After U251MG cells were infected with the type-2 AAV vector, the number of intracellular genome copies was measured in a time-course manner (0, 2, 4, 12, and 24 hours). No significant difference was observed in the genome copy number between an FK228-treated group and a control group (only a solvent), although a slight increase in the genome copy number was observed in the FK228-treated group 24 hours after the infection. The results are shown in FIG. 2.

The results indicate that the effect of FK228 in enhancing transgene expression is not mediated by an increase in the number of genome copies in cells.

INDUSTRIAL APPLICABILITY

The gene transfer efficiency enhancer of the present invention, which contains a histone deacetylase inhibitor (in particular, compound A or a salt thereof, which has histone deacetylase inhibitory activity), exhibits an excellent effect of increasing the efficiency of adeno-associated-virus-vector-mediated gene transfer into tumor cells, which gene transfer efficiency has conventionally been shown to be low. Therefore, the gene transfer efficiency enhancer can be suitably employed in clinical practice, particularly for gene therapy, more particularly for cancer gene therapy.

Sequence Listing Free Text

SEQ ID NO: 1: Xaa denotes an amino acid represented by the formula: $NH_2C(CHCH_3)COOH$.

The carboxyl group of a compound $COOHCH_2CH(CHCHC_2H_4SH)OH$ is bonded to the amino group of the first amino acid (Val); the hydroxyl group of the compound is bonded to the carboxyl group of the fourth amino acid (Val); and the SH group of the compound forms a disulfide bond with the SH group of the second amino acid (Cys).

The present application is based on Japanese Patent Application 2003-122968, the content of which is incorporated herein by reference in its entirety.

SEQUENCE LISTING

<160> NUMBER OF SEQ ID NOS: 1

<210> SEQ ID NO 1
<211> LENGTH: 4
<212> TYPE: PRT
<213> ORGANISM: Chromobacterium sp.
<220> FEATURE:
<221> NAME/KEY: SITE
<222> LOCATION: (1)..(1)
<223> OTHER INFORMATION: In the formula COOHCH2CH(CHCHC2H4SH)OH, the
      carboxylic group is bonded with the amino group of the first
      amino acid Val.
<220> FEATURE:
<221> NAME/KEY: SITE
<222> LOCATION: (2)..(2)
<223> OTHER INFORMATION: In the formula COOHCH2CH(CHCHC2H4SH)OH, the SH
      group is bonded with the SH group of the second amino acid Cys
      via a disulfide bond.
<220> FEATURE:
<221> NAME/KEY: SITE
<222> LOCATION: (3)..(3)
<223> OTHER INFORMATION: Xaa is any naturally occurring amino acid.
<220> FEATURE:
<221> NAME/KEY: SITE
<222> LOCATION: (4)..(4)
<223> OTHER INFORMATION: In the formula COOHCH2CH(CHCH2H4SH)OH, the
      hydroxyl group is bonded with the carboxylic group of the fourth
      amino acid Val.

<400> SEQUENCE: 1

Val Cys Xaa Val
1

The invention claimed is:

1. A method for increasing transgene expression in a gene transfer mediated by an adeno-associated virus vector (AAV), comprising:
    administering (a) an AAV comprising a transgene and (b) an effective dose of a histone deacetylase inhibitor to a human subject in need thereof, wherein:
    the histone deacetylase inhibitor is a compound represented by formula (I):

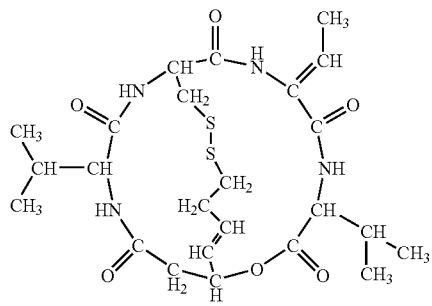

(I)

or a salt or a derivative of the compound; and
the effective dose of a histone deacetylase inhibitor is an amount that results in increased expression of the transgene.

2. The method of claim 1, wherein the histone deacetylase inhibitor is administered before administration of the adeno-associated virus vector.

3. The method of claim 1, wherein the subject is an adult and the effective dose of the histone deacetylase inhibitor is 1 mg/m$^2$ to 50 mg/m$^2$ of a compound represented by formula (I):

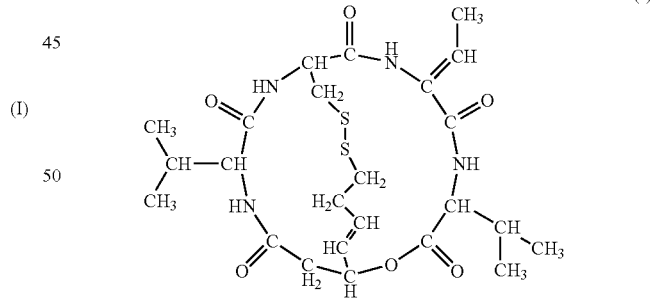

(I)

or a salt or a derivative of the compound daily.

4. The method of claim 1, wherein the AAV comprising a transgene and the histone deacetylase inhibitor are administered to tumor cells.

5. The method of claim 4, wherein the method is performed for gene therapy, and the subject has cancer.

6. The method of claim 1, wherein the method is performed for gene therapy and the subject has cancer; a neuromuscular disease; myotonic dystrophy; amyotrophic lateral sclerosis (ALS); heart failure; cardiomyopathy; diseases treated with protein supplementation therapy through expression of a secretory protein; chronic systemic diseases; arteriosclerosis; hypertension; heart failure; diabetes; hyperlipidemia; cerebral infarction; reperfusion injury after cerebral ischemia; Parkinson's disease; various neurodegenerative disease; mitochondrial encephalomyopathy; epilepsy; schizophrenia; or alcoholism.

7. A method for increasing the efficiency of a transduction mediated by an adeno-associated virus vector (AAV), comprising: administering (a) an AAV comprising a transgene and (b) an effective amount of a histone deacetylase inhibitor to human cells in need thereof, wherein:

the histone deacetylase inhibitor is a compound represented by formula (I):

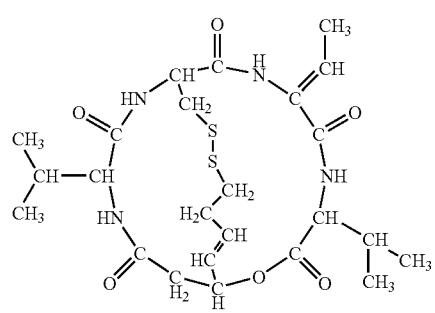

(I)

or a salt or a derivative of the compound; and the effective dose of a histone deacetylase inhibitor is an amount that results in increased transduction efficiency.

8. The method claim 7, wherein the AAV comprising a transgene and the histone deacetylase inhibitor are administered to embryonic stem cells or hematopoietic stem cells.

9. The method as described in claim 7, wherein the cells are tumor cells of a subject.

10. The method as described in claim 7, wherein the histone deacetylase inhibitor is a compound represented by the formula (I):

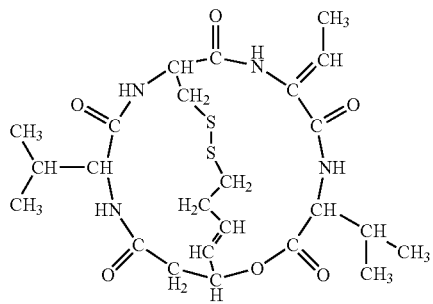

(I)

or a salt or a derivative of the compound.

11. The method according to claim 7,
wherein the cells are tumor cells of a subject, and
wherein the histone deacetylase inhibitor is a compound represented by the formula (I):

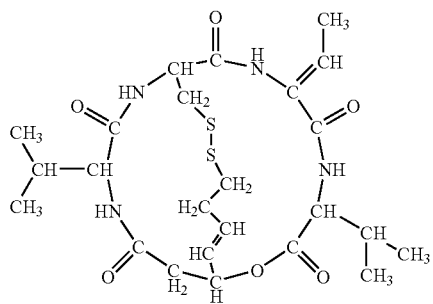

(I)

or a salt or a derivative of the compound.

12. The method of claim 1, wherein the histone deacetylase inhibitor is FK228.

13. The method of claim 7, wherein the histone deacetylase inhibitor is FK228.

14. The method of claim 1, wherein the derivative is obtained through acetylation of the compound or through reduction of the S—S bond of the compound.

15. The method of claim 7, wherein the derivative is obtained through acetylation of the compound or through reduction of the S—S bond of the compound.

* * * * *